(12) United States Patent
Honda et al.

(10) Patent No.: US 6,616,608 B2
(45) Date of Patent: Sep. 9, 2003

(54) PERIODIC-PHYSICAL-INFORMATION MEASURING APPARATUS

(75) Inventors: Takashi Honda, Komashi (JP); Toshihiko Ogura, Komashi (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/749,386

(22) Filed: Dec. 28, 2000

(65) Prior Publication Data

US 2001/0008953 A1 Jul. 19, 2001

(30) Foreign Application Priority Data

Jan. 13, 2000 (JP) .......................................... 2000-04117

(51) Int. Cl.⁷ ...................... A61B 5/0205; A61B 5/0285
(52) U.S. Cl. ........................ 600/301; 600/481; 600/529
(58) Field of Search ................................ 600/300, 301, 600/481, 483, 485, 500, 529, 490, 493, 494; 128/902, 903, 904, 905, 920, 923

(56) References Cited

U.S. PATENT DOCUMENTS

| | | | |
|---|---|---|---|
| 4,379,460 A | 4/1983 | Judell | 600/484 |
| 4,860,759 A | 8/1989 | Kahn et al | 600/481 |
| 5,178,154 A | 1/1993 | Ackmann et al. | 600/526 |
| 5,462,051 A | * 10/1995 | Oka et al. | 600/300 |
| 5,980,463 A | 11/1999 | Brockway et al. | 600/485 |
| 6,027,453 A | * 2/2000 | Miwa et al. | 600/485 |
| 6,322,516 B1 | * 11/2001 | Masuda et al. | 600/493 |
| 6,383,136 B1 | * 5/2002 | Jordan | 600/300 |

FOREIGN PATENT DOCUMENTS

| | | |
|---|---|---|
| JP | B-51-5231 | 2/1976 |
| JP | A-7-367 | 1/1995 |
| JP | A-7-275219 | 10/1995 |
| JP | A-7-284482 | 10/1995 |
| JP | A-7-313477 | 12/1995 |
| JP | A-54-120997 | 9/1997 |
| WO | WO 85/00099 | 1/1985 |

* cited by examiner

*Primary Examiner*—Willis R. Wolfe
(74) *Attorney, Agent, or Firm*—Oliff & Berridge, PLC

(57) ABSTRACT

An apparatus for measuring a periodic physical information of a living subject, including a measuring device which iteratively measures, from the subject, a value of the periodic physical information including a periodically changing component, a waveform determining device for determining a changing-component waveform representing the periodically changing component of the periodic physical information, a difference determining device for determining at least one difference between at least one first value of the periodic physical information measured by the measuring device at at least one time and at least one second value of the changing-component waveform at the at least one time, and a removing device for judging, based on the at least one difference determined by the difference determining device, whether the at least one first value is abnormal, and removing the at least one first value judged as being abnormal.

10 Claims, 10 Drawing Sheets

PERIODIC-PHYSICAL-INFORMATION MEASURING APPARATUS

BACKGROUND OF THE INVENTION

1. Field of the Invention

The present invention relates to an apparatus for iteratively measuring a value of a periodic physical information including a periodically changing component and removing one or more abnormal values from the iteratively measured values of the periodic physical information.

2. Discussion of Related Art

When a sort of physical information is obtained or measured from a patient, for the purpose of diagnosing a disease of the patient or monitoring a physical condition of the patient, the physical information is often measured continuously to improve the accuracy of measurement or find any significant change of the information during the measurement.

For example, a degree of arteriosclerosis may be diagnosed based on a pulse-wave propagation velocity at which a pulse wave propagates through an artery of a patient. The measurement of pulse-wave propagation velocity needs to measure a pulse-wave propagation time needed for the pulse wave to propagate from a first portion, to a second portion, of the artery. To this end, a rising or start point of a second heart sound, II, detected by a heart-sound sensor from the heart of the patient may be used as a first or upstream-side point to measure the pulse-wave propagation time. Here, the accuracy of detection of the start point of the second heart sound II may be improved by detecting respective start points of a plurality of second heart sounds II and calculating an average of the detected start points. More specifically described, first, respective time durations from respective reference waves to respective start points of a plurality of second heart sounds II are measured, and then an average of those time durations is calculated. For example, the reference waves may be respective R waves of an electrocardiogram (ECG) whose waveform can be clearly detected. That is, respective time durations, R-II, from respective R waves of ECG waveform to respective start points of second heart sounds II are measured, and then an average of those time durations R-II is calculated. Thus, the measurement of pulse-wave propagation velocity may need to iteratively measure, in advance, the time durations R-II as a sort of physical information of the patient.

However, the second heart sounds II detected by the heart-sound sensor are easily mixed with noise. Therefore, the time durations R-II measured as described above may include one or more aberrant or abnormal values produced by the noise. In addition, not only the second heart sound II but also other sorts of physical information obtained from a living subject are easily mixed with noise. Thus, the measured values of each sort of physical information may include one or more abnormal values resulting from the occurrence of one or more errors during the measurement. In addition, there is a need to finish the measurement in a short time to reduce the burden exerted to the patient. To this end, the total number of measured values of the physical information should be as small as possible. However, if the small number of measured values include one abnormal value, it may adversely influence a diagnosis to be made for the patient.

Here, it is possible to make a graph showing a distribution of the measured values of physical information, judge one or more values largely deviated from the distribution, as being abnormal, and remove the values judged as abnormal.

However, there is known a periodic physical information having a periodically changing component. Even if the measured values of periodic physical information may include one or more abnormal values resulting from erroneous measurement, the abnormal value or values may not be largely deviated from the distribution of measured values and may not be Judged as being abnormal, or removed. FIGS. 10A and 10B show abnormal values which cannot be discriminated or removed. More specifically described, FIG. 10A shows a graph representing respective values of periodic physical information that are iteratively measured as time elapses. An axis of abscissa is indicative of the time, and an axis of ordinate is indicative of the magnitude or value of periodic physical information. Circles 80 indicate correctly measured values of periodic physical information, a cross 82 indicates an abnormal value resulting from erroneous measurement. A periodic curve, C, represents a waveform of the periodically changing component of the periodic physical information.

FIG. 10B shows a histogram representing the respective measured values of periodic physical information. The abnormal value indicated by the cross 82 in FIG. 10A is located at an outermost end of the distribution shown in FIG. 10B, but is not clearly deviated from the other measured values. Thus, it is difficult to find and discard the abnormal value 82. In addition, in FIG. 10A, a triangle 84 also indicates an abnormal value which, however, falls within the periodic change of the physical information. Since this abnormal value is mixed with the normal celio values in the histogram shown in FIG. 10B, it cannot be found or discarded. Thus, it has been difficult to discard one or more abnormal values from the measured values of any sort of periodic physical information.

SUMMARY OF THE INVENTION

It is therefore an object of the present invention to provide a periodic-physical-information measuring apparatus which iteratively measures a value of periodic physical information and which can easily remove one or move abnormal values from the iteratively measured values of periodic physical information.

The present invention provides a periodic-physical-information measuring apparatus which has one or more of the following technical features that are described below in respective paragraphs given parenthesized sequential numbers (1) to (6). Any technical feature that includes another technical feature shall do so by referring, at the beginning, to the parenthesized sequential number given to the latter feature.

However, the following technical features and the appropriate combinations thereof are just examples to which the present invention is by no means limited.

(1) According to a first feature of the present invention, there is provided an apparatus for measuring a periodic physical information of a living subject, comprising a measuring device which iteratively measures, from the subject, a value of the periodic physical information comprising a periodically changing component; a waveform determining means for determining a changing-component waveform representing the periodically changing component of the periodic physical information; a difference determining means for determining at least one difference between at least one first value of the periodic physical information measured by the measuring device at at least one time and at least one second value of the changing-component waveform at the at least one time; and a removing means for judging, based on the at least one difference determined by the difference determining means, whether the at least one first value is abnormal, and removing the at least one first value judged as being abnormal.

In the present periodic-physical-information measuring apparatus, the measuring device measures values of the periodic physical information, the waveform determining means determines the changing-component waveform representing the periodically changing component of the periodic physical information measured by the measuring device, the difference determining means determines a difference between a first value of the periodic physical information measured by the measuring device at a time and a second value of the changing-component waveform at that time, and the removing means judges, based on the determined difference, whether the first value is abnormal, and removes the first value of the periodic physical information that is judged as being abnormal. Thus, the present apparatus can easily remove one or more abnormal values from the iteratively measured values of periodic physical information.

(2) According to a second feature of the present invention that includes the first feature (1), the measuring apparatus further comprises an average determining means for determining an average of the iteratively measured values of the periodic physical information from which the at least one first value judged as being abnormal has been removed. In the present measuring apparatus, the average determining means determines an average of the iteratively measured values of the periodic physical information from which the one or more first values judged as being abnormal has or have been removed. This average is more accurate than an average of the values of periodic physical information from which no abnormal values have been removed.

(3) According to a third feature of the present invention, there is provided an apparatus for measuring a periodic physical information of a living subject, comprising a measuring device which iteratively measures, from the subject, a value of the periodic physical information comprising a periodically changing component resulting from a respiration of the subject; a respiration-wave detecting device which detects a respiration wave resulting from the respiration of the subject; a waveform determining means for determining, based on the respiration wave detected by the respiration-wave detecting device, a changing-component waveform representing the periodically changing component of the periodic physical information; a difference determining means for determining at least one difference between at least one first value of the periodic physical information measured by the measuring device at at least one time and at least one second value of the changing-component waveform at the at least one time; and a removing means for judging, based on the at least one difference determined by the difference determining means, whether the at least one first value is abnormal, and removing the at least one first value judged as being abnormal.

In the present periodic-physical-information measuring apparatus, the measuring device measures respective values of the periodic physical information containing the periodically changing component resulting from the respiration of the subject, the respiration-wave detecting device detects the respiration wave resulting from the respiration of the subject, the waveform determining means determines, based on the respiration wave, the changing-component waveform representing the periodically changing component of the periodic physical information, the determining means determining a difference between a first value of the periodic physical information measured at a time and a second value of the changing-component waveform at that time, and the removing means judges, based on the determined difference, whether the first value is abnormal, and removes the first value of the periodic physical information that is judged as being abnormal. Thus, the present apparatus can easily remove one or more abnormal values from the iteratively measured values of periodic physical information containing the periodically changing component resulting from the respiration of the subject.

(4) According to a fourth feature of the present invention that includes the third feature (3), the measuring apparatus further comprises an average determining means for determining an average of the iteratively measured values of the periodic physical information from which the at least one first value judged as being abnormal has been removed. In the present measuring apparatus, the average determining means determines an average of the iteratively measured values of the periodic physical information from which the one or more values judged as being abnormal has or have been removed. This average is more accurate than an average of the iteratively measured values of periodic physical information from which no abnormal values have been removed.

(5) According to a fifth feature of the present invention that includes the third or fourth features (3) or (4), the respiration-wave detecting device comprises a chest-impedance-pulse-wave detecting device which detects a chest-impedance pulse wave from a chest of the subject; and an extracting means for extracting the respiration wave from the chest-impedance pulse wave detected by the chest-impedance-pulse-wave detecting device. Since the chest-impedance pulse wave detected by the chest-impedance-pulse-wave detecting device contains a respiration-synchronous component, the extracting means extracts, as an accurate respiration wave, the respiration-synchronous component from the chest-impedance pulse wave.

(6) According to a sixth feature of the present invention that includes any one of the third to fifth features (3) to (5), the measuring device comprises an electrocardiograph device which includes a plurality of electrodes adapted to be placed on a plurality of body portions of the subject, continuously detects an electrocardiogram waveform, from the subject through the electrodes, and outputs an electrocardiogram-waveform signal representing the detected electrocardiogram waveform; a heart-sound sensor which detects a plurality of second heart sounds, II, produced from the heart of the subject, and outputs a heart-sound signal representing the detected second heart sounds II; and a measuring means for iteratively measuring a time difference between a first time when a predetermined periodic point on the electrocardiogram waveform is detected by the electrocardiograph device and a second time when a start point of each of the second heart sounds II is detected by the heart-sound sensor. In the case where the above-described average determining means determines an average of the iteratively measured time differences from which one or more abnormal time differences have been removed, the thus determined average is more accurate than an average of the iteratively measured time differences from which no abnormal time differences have been removed. In addition, since the electrocardiogram waveform is not easily mixed with noise and accordingly is accurately detected, the average of the time differences measured based on the electrocardiogram waveform provides an accurate time when the second heart sound II occurs as measured from the predetermined periodic point on the electrocardiogram waveform

BRIEF DESCRIPTION OF THE DRAWINGS

The above and other objects, features, advantages and technical and industrial significance of the present invention will be better understood by reading the following detailed description of preferred embodiments of the invention, when considered in connection with the accompanying drawings, in which.

DETAILED DESCRIPTION OF PREFERRED EMBODIMENTS

Figure 1:
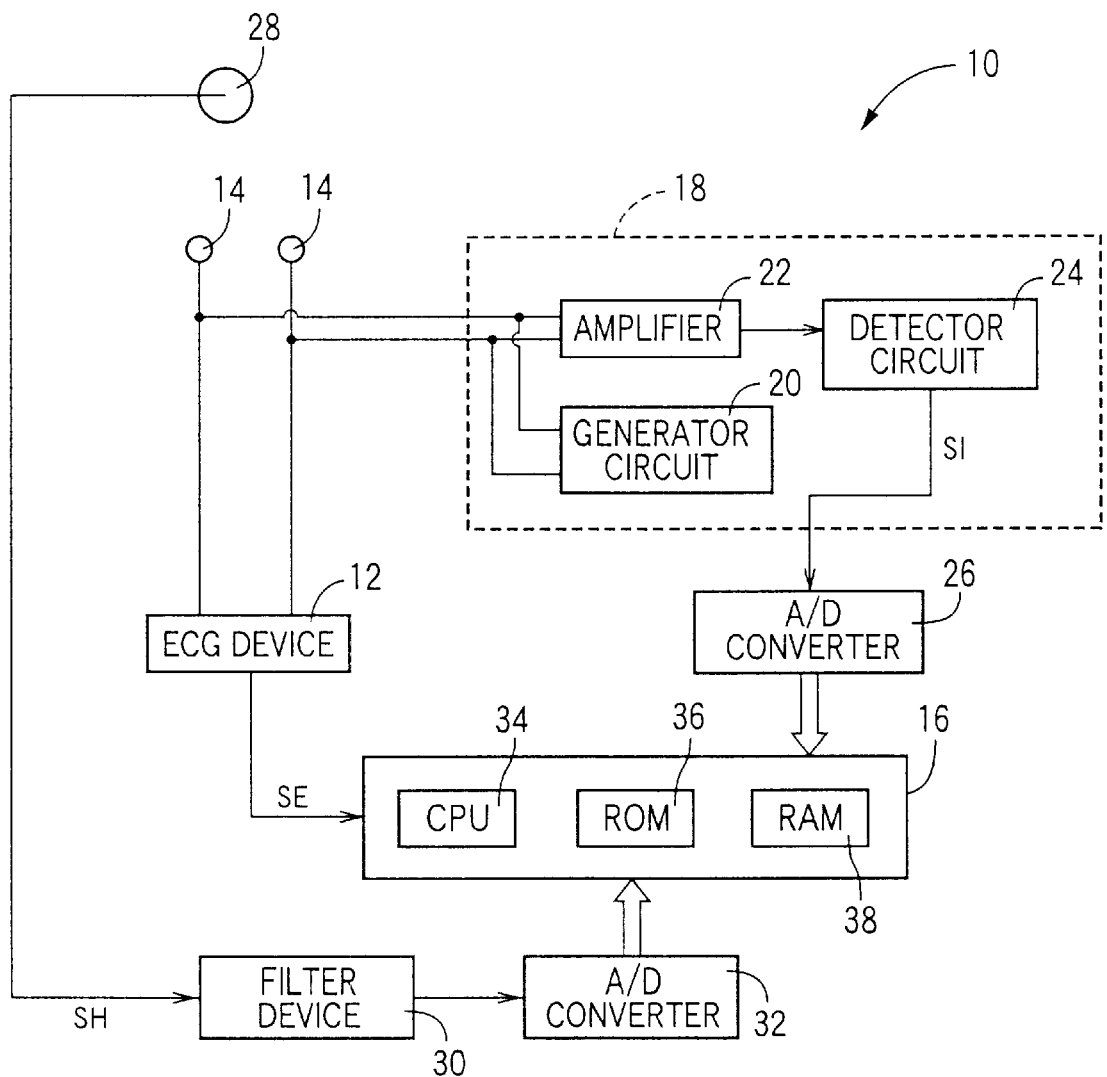
FIG. 1 is a diagrammatic view of the construction of a periodic-physical-information measuring apparatus to which the present invention is applied.

Hereinafter, there will be described one embodiment of the present invention, by reference to the accompanying drawings. FIG. 1 is a diagrammatic view of a construction of a periodic-physical-information measuring apparatus 10 to which the present invention is applied.

In FIG. 1, an electrocardiograph (ECG) device 12 includes two electrodes 14 which are adapted to be placed on the skin of chest of a living subject, and continuously detects, through the electrodes 14, an electrocardiogram (ECG) waveform representing an action potential of the cardiac muscle of the subject. The ECG device 12 supplies an ECG signal, SE, representing the detected ECG waveform, to a control device 16 via an analog-to-digital (A/D) converter (not shown).

A chest-impedance detecting device 18 includes a plurality of electrodes which are adapted to be placed on the chest of the subject, and continuously detects, through the electrodes, an impedance of the chest of the subject, i.e., a chest-impedance pulse wave. In the present embodiment, the electrodes of the chest-impedance detecting device 18 are provided by the electrodes 14 of the ECG device 12. The detecting device 18 includes a generator circuit 20 which generates a sinusolidal current having a predetermined frequency (e.g., 50 Hz) and applies the electric current to the subject; an amplifier 22 which amplifies the signal detected through the electrodes 14; and a detector circuit 24 which extracts, from the amplified signal, a chest-impedance signal, SI, representing the detected chest-impedance pulse wave. The detecting device 18 supplies the chest-impedance signal SI to the control device 16 via an A/D converter 26.

A heart-sound microphone 28 as a heart-sound sensor is adapted to be placed, on the skin of center of the chest of the subject, at a predetermined heart-sound-detection position right above the apex of the heart, the left end of the fourth intercostal sternum, the left end of the second intercostal sternum, the right end of the second intercostal sternum, or the right end of the fourth intercostal sternum, and detects airborne heart sounds of the subject. The heart-sound microphone 28 supplies a phonocardiogram (PCG) signal, SH, representing the detected heart sounds, i.e., phonocardiogram (PCG) waveform, to the control device 16 via a filter device 30, an A/D converter 32 and an amplifier (not shown).

Figure 3:
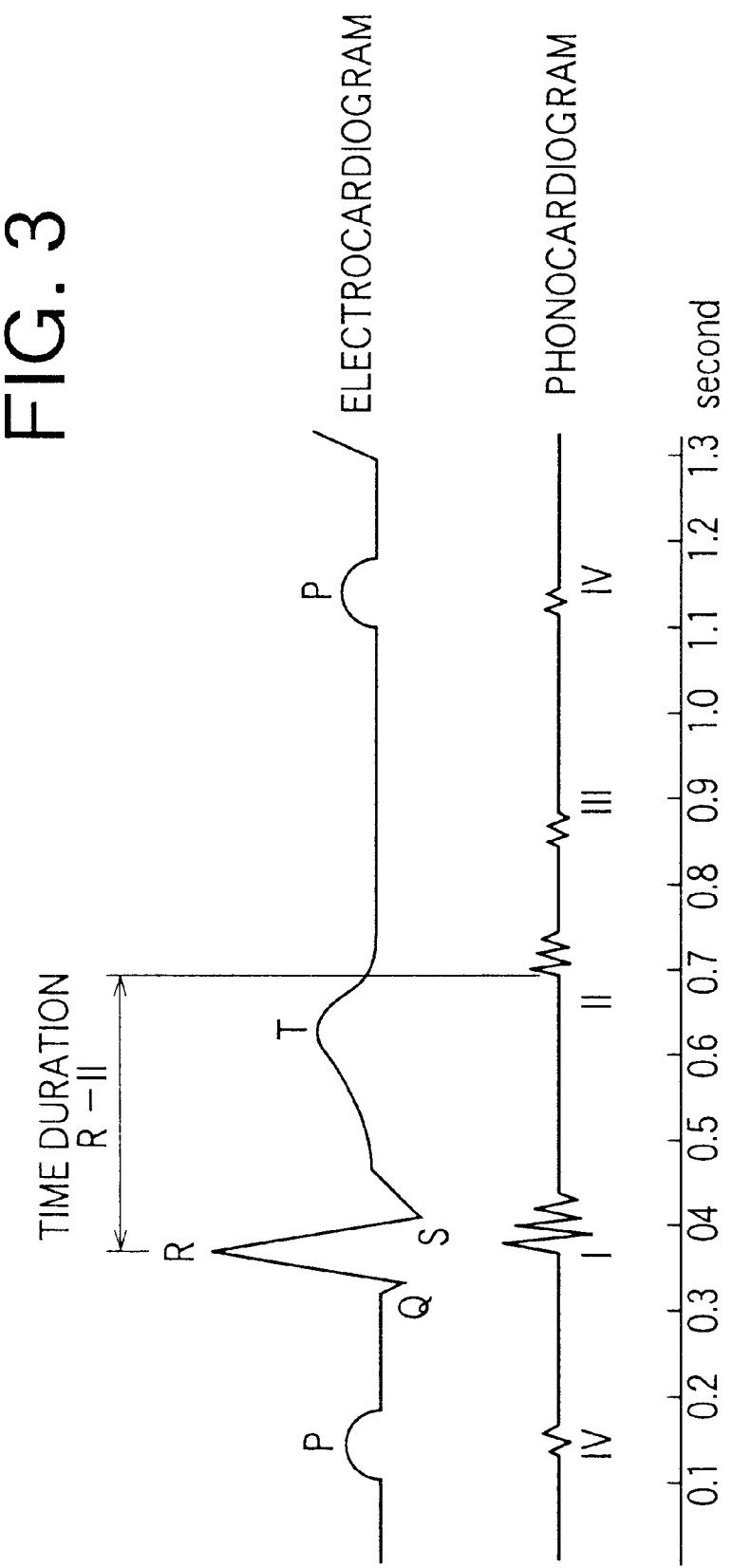
FIG. 3 is a view for explaining a time duration, R-II, which is measured by a time-duration (R-II) measuring means shown in FIG. 2.

The filter device 30 includes four sorts of filters (not shown) corresponding to four sorts of heart sounds, I, II, III, and IV, shown in FIG. 3, and sequentially selects each of the four filters for filtering out a corresponding one of the four sorts of heart sounds. Each of the four filters attenuates low-frequency components of the PCG signal SH, and thereby emphasizes high-frequency components of the same SH, so that the heart sounds represented by the filtered signal SH may be heard by the auditory organ of a human being such as a doctor or a nurse.

The control device 16 is essentially provided by a so-called microcomputer including a central processing unit (CPU) 34, a read only memory (ROM) 36, a random access memory (RAM) 38, and an input-and-output (I/O) port (not shown). The CPU 34 processes the ECG signal SE, the chest-impedance signal SI, and the PCG signal SH supplied thereto, by utilizing a temporary-storage function of the RAM 38, according to a control program pre-stored in the ROM 36, and iteratively calculates respective time durations, R-II, as respective values of periodic physical information, determines a respiration wave, and removes, based on the determined respiration wave, one or more abnormal time durations R-II from the iteratively calculated time durations R-II, as described below.

Figure 2:
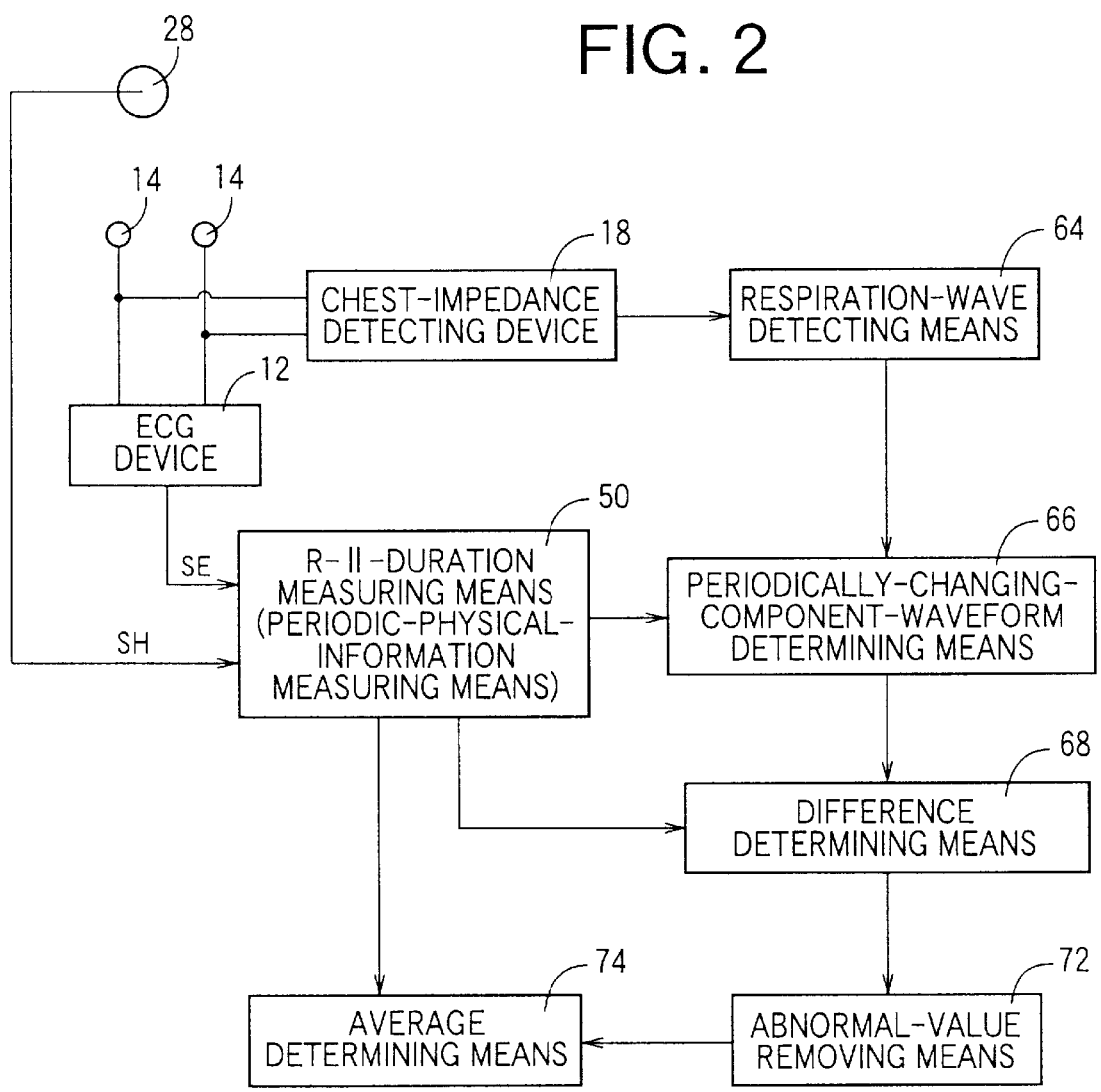
FIG. 2 is a block diagram for explaining various functions of a control device of the apparatus of FIG. 1.

FIG. 2 is a block diagram for explaining various control functions of the control device 16 of the periodic-physical-information measuring apparatus 10 constructed as described above. In FIG. 2, an R-II-duration measuring means 50 iteratively measures, in a predetermined interval, a time duration R-II from a time when a predetermined periodic point, i.e., an R-wave is detected on the ECG waveform represented by the ECG signal SE, and a time when a predetermined periodic point, i.e., a start point of second heart sound II is detected on the PCG waveform represented by the PCG signal SH, as shown in FIG. 3. The R-wave is one of the most accurately and easily detectable waves of the ECG waveform. The predetermined interval is a time corresponding to 30 beats of the heart of the subject, i.e., 30 R-waves of the ECG waveform.

Figure 4:
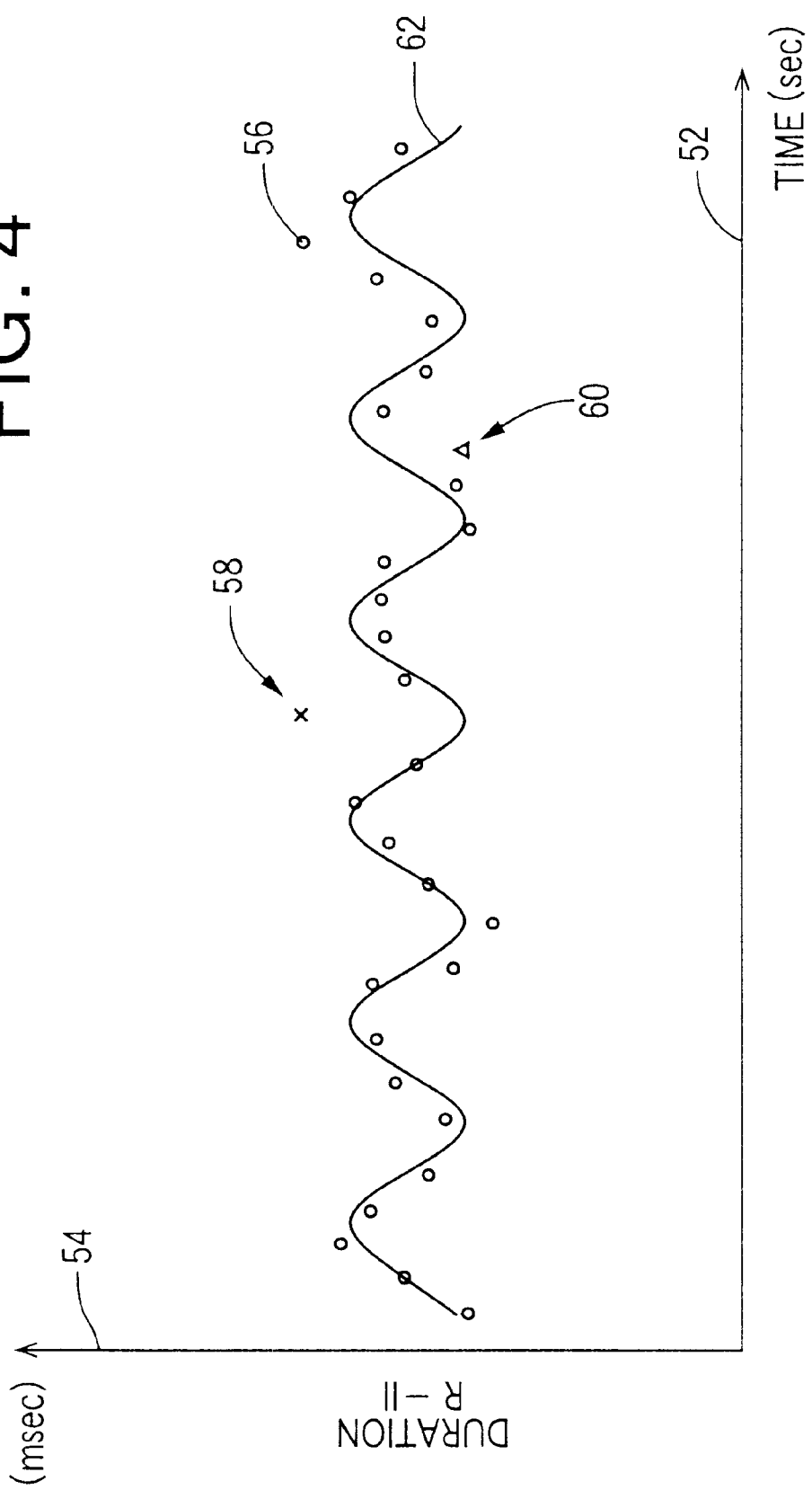
FIG. 4 is a graph showing thirty time durations R-II corresponding to thirty beats the heart of a living subject.

FIG. 4 is a graph showing a time-wise changes of the 30 time durations R-II iteratively measured by the R-II-duration measuring means 50. An axis of abscissa 52 is indicative of time, i.e., respective times when the time durations R-II are measured; and an axis of ordinate is indicative of time duration R-II, i.e., respective lengths of the measured time durations R-II. Circles 56 indicate normal time durations R-II, and a cross 58 and a triangle 60 indicate respective abnormal time durations R-II. A periodic curve 62 indicates a waveform of a periodically changing component, M, which is contained in the measured time durations R-II and which is determined by a periodically-changing-component-waveform determining means 66, described later. However, it is noted that, in fact, the time durations R-II indicated by the cross 58 and the triangle 60 in FIG. 4 cannot be discriminated from the time durations R-II indicated by the circles 56, in this graph. That is, the time durations R-II may, or may not, include one or more abnormal time durations R-II as indicated by the cross 58 and the triangle 60.

The second heart sound II is produced each time the aortic valve is closed, and the respective time durations R-II between the respective R-waves of the ECG waveform and the corresponding second heart sounds II, iteratively measured by the measuring means 50, contain a periodically changing component resulting from the respiration of the subject. Thus, the time durations R-II are values of periodic physical information containing a periodically changing component resulting from respiration of a living subject. In the present embodiment, the R-II-duration measuring means 50 provides a periodic-physical-information measuring means.

Figure 5:
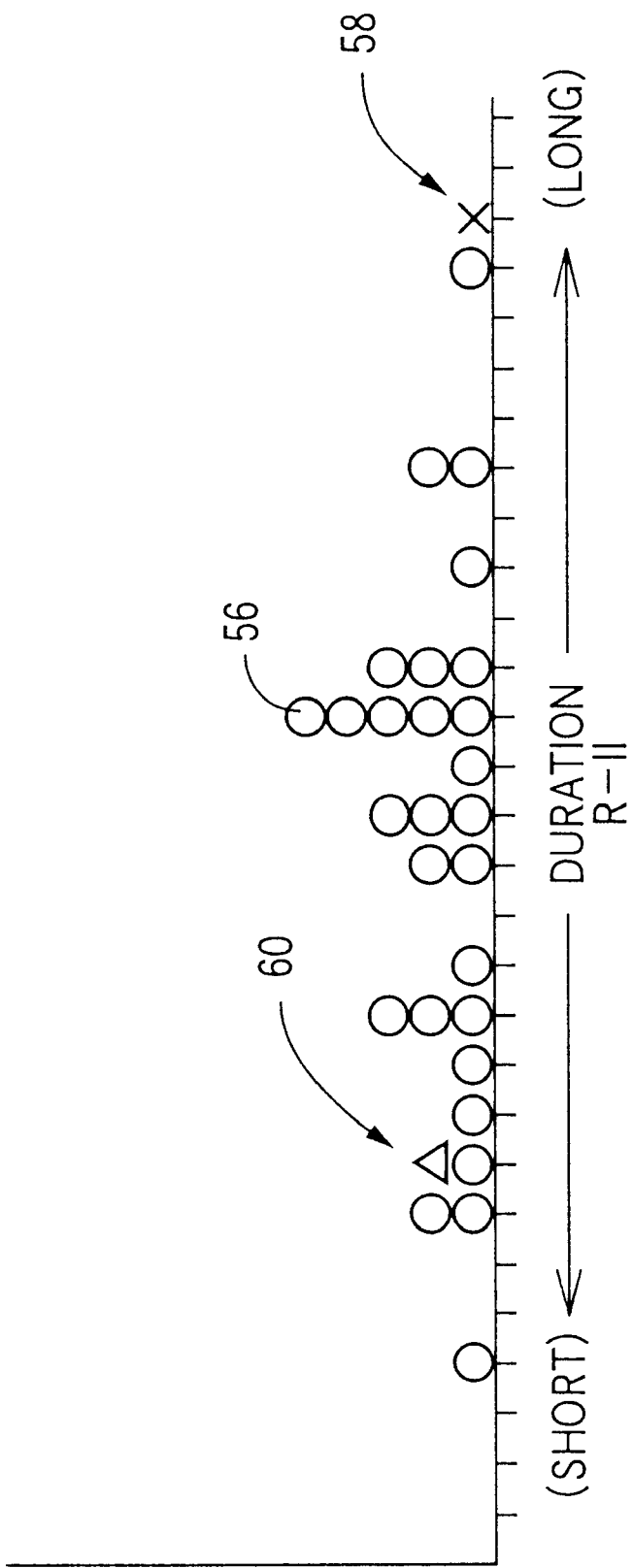
FIG. 5 is a graph showing a distribution of the thirty time durations R-II shown in FIG. 4.

FIG. 5 is a graph showing a distribution of the respective lengths of the 30 time durations R-II shown in the graph of FIG. 4. In FIG. 5, the abnormal time duration R-II indicated by the cross 58 is adjacent to the normal time durations R-II indicated by the circles 56, and the abnormal time duration R-II indicated by the triangle 60 is mixed with the normal time durations R-II indicated by the circles 56. Thus, it is difficult to discriminate, in this graph, the abnormal durations R-II indicated by the cross 58 and the triangle 60, from the normal durations R-II indicated by the circles 56.

Figure 6:
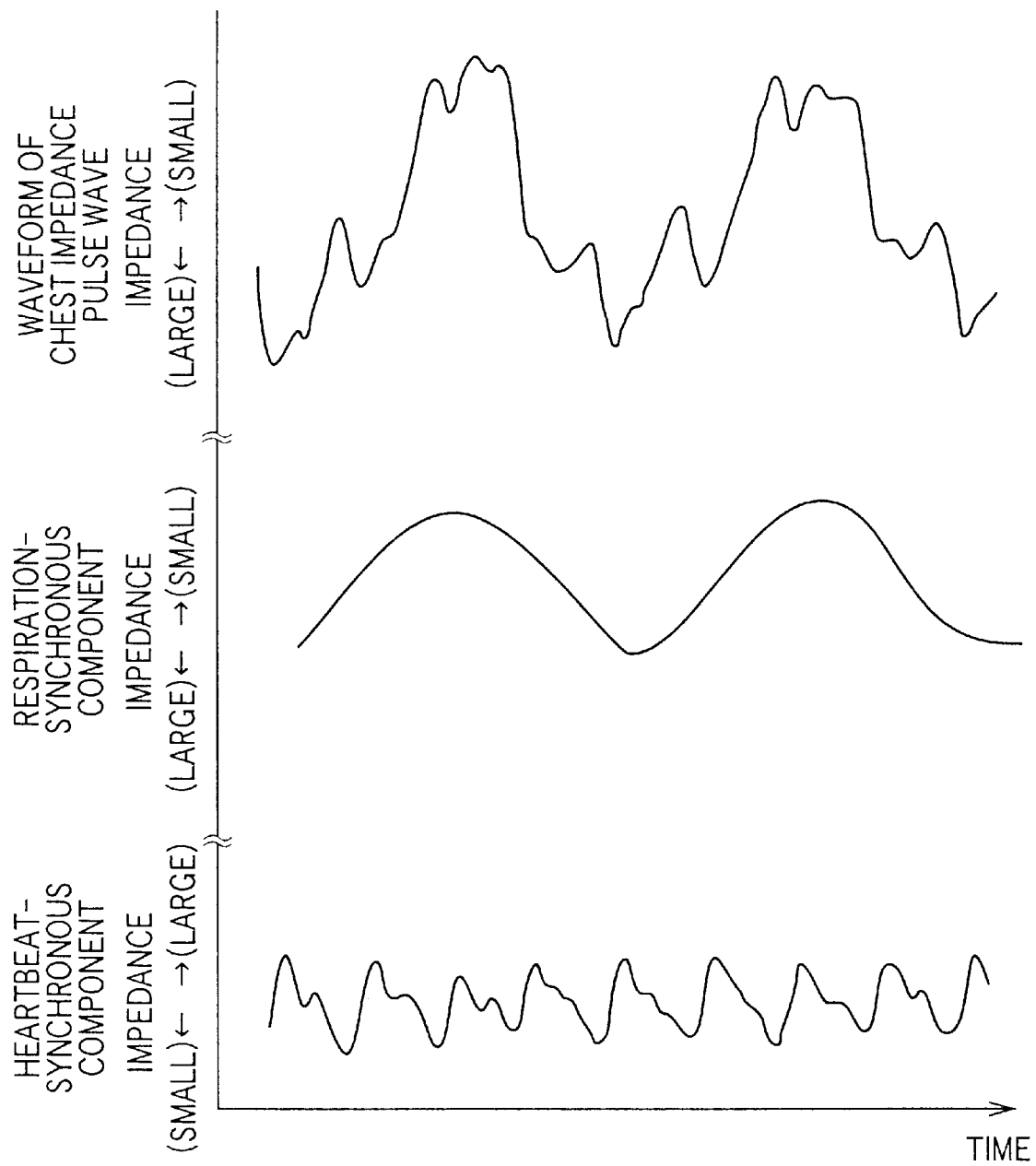
FIG. 6 is a graph showing a chest-impedance pulse wave which is detected by a chest-impedance-pulse-wave detecting device shown in FIG. 1, and a respiration-synchronous component and a heartbeat-synchronous component contained in the chest-impedance pulse wave.

A respiration-wave detecting means 64 continuously detects a respiration wave from the chest-impedance signal SI supplied from the chest-impedance detecting device 18. A top portion of FIG. 6 is a graph showing the waveform of chest-impedance pulse wave represented by the chest-impedance signal SI. The waveform of chest-impedance pulse wave contains a heartbeat-synchronous component corresponding to the time-wise change of volume of blood present in the heart, shown in a middle portion of FIG. 6, and a respiration-synchronous component corresponding to the time-wise change of volume of air present in the chest, shown in a bottom portion of FIG. 6. The respiration-wave detecting means 64 functions as an extracting means for extracting, from the chest-impedance signal SI, a respiration-synchronous component having frequencies in a predetermined frequency band of from 0.1 to 0.5 Hz, and adopting the thus extracted component as the respiration wave. It is noted that in the top and middle graphs of FIG. 6, the impedance decreases in an upward direction along the axis of ordinate and, in the bottom graph of FIG. 6, the impedance increases in the upward direction.

The periodically-changing-component-waveform (PCCW) determining means 66 determines, based on the respiration wave detected by the respiration-wave detecting means 52, the waveform of the periodically changing component M contained in the time durations R-II that results from the respiration of the subject. A cycle or period of the periodically changing component M contained in the time durations R-II measured by the R-II-duration measuring means 50 can be thought to coincide with that of the respiration wave detected by the respiration-wave detecting means 52. Assuming that the respiration wave continuously detected by the respiration-wave detecting means 52 is expressed as f(t), the periodically changing component M can be expressed by the following expression (1):

$$M = \alpha f(t) + \beta \quad (1)$$

where $\alpha$ and $\beta$ are constants.

The two constants $\alpha$, $\beta$ of the expression (1) are so determined that the sum of respective squares of respective differences between respective values of the 30 time durations R-II measured at respective times and respective values of the periodically changing component M at the corresponding times takes the least value. The periodic curve 62 shown in FIG. 4 indicates the waveform of periodically changing component M determined in this manner.

A difference determining means 68 determines a difference, $\Delta A$, between the value of each of the 30 time durations R-II measured at a time and the value of a corresponding one of the periodically changing component M (i.e., the periodic curve 62) at the same time. Thus, the difference determining means 68 determines the 30 differences $\Delta A$ shown in the graph of FIG. 7. An axis of abscissa 52 of this graph is common to the axis of abscissa 52, shown in FIG. 4, that is indicative of time, and an axis of ordinate of this graph is indicative of difference $\Delta A$.

Figure 7:
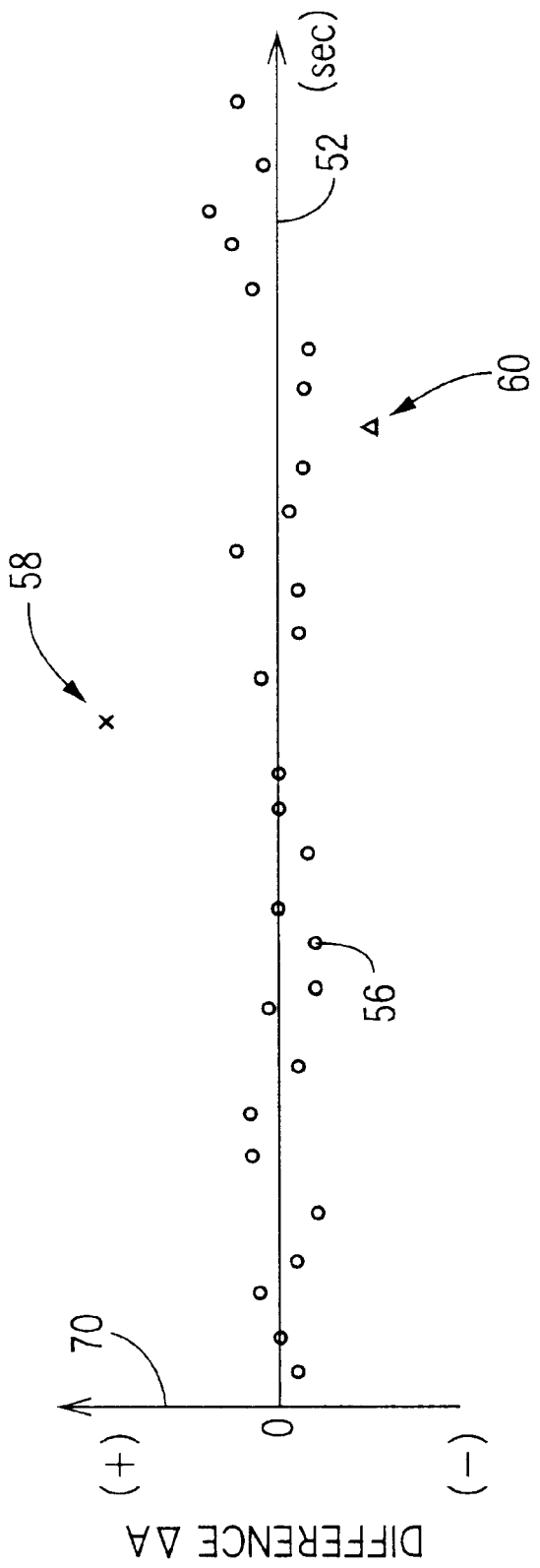
FIG. 7 is a graph showing thirty differences, ΔA, which are determined by a difference determining means shown in FIG. 2.
Figure 8:
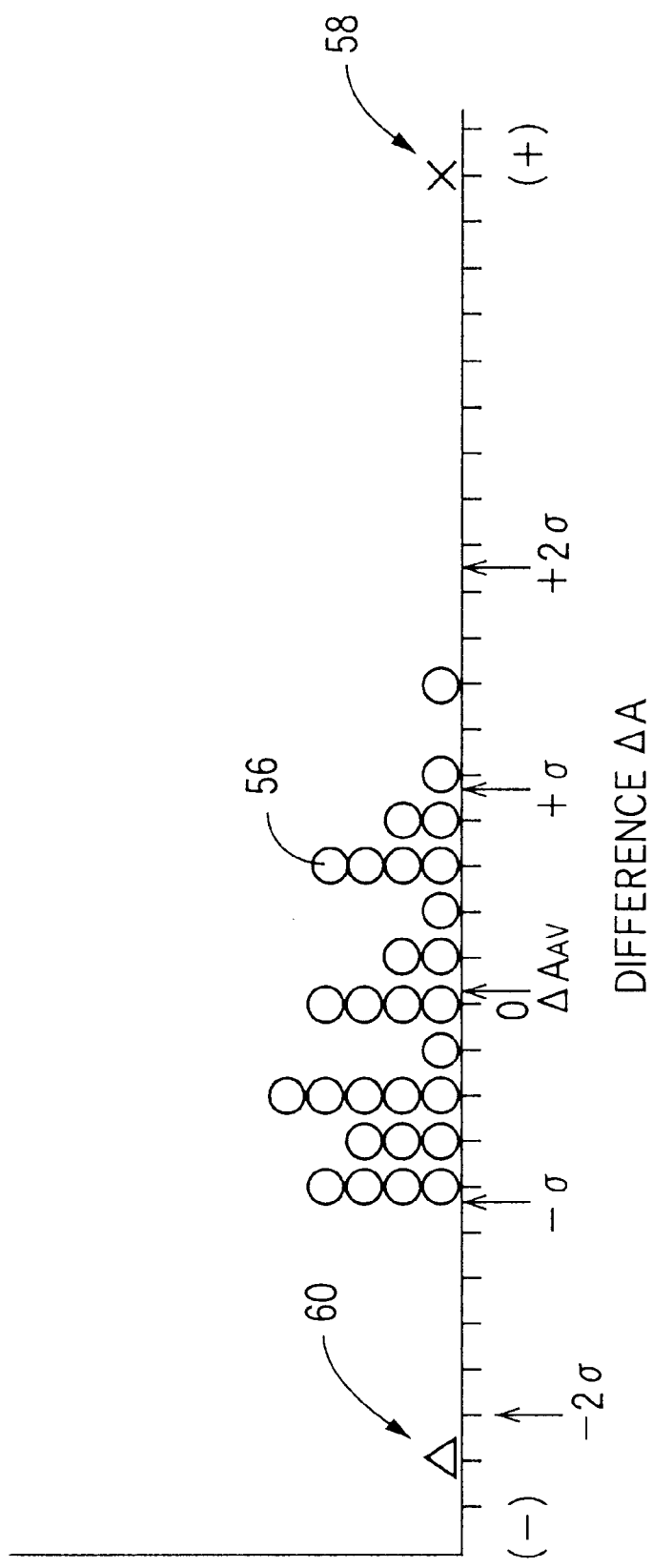
FIG. 8 is a graph showing a distribution of the thirty differences ΔA shown in FIG. 7.

FIG. 8 is a graph showing a distribution of the 30 differences $\Delta A$ shown in FIG. 7. In this graph, the abnormal time durations R-II indicated by the cross 58 and the triangle 60 are largely deviated from the normal time durations R-II indicated by the circles 56.

An abnormal-value removing means 72 finds, based on the differences $\Delta A$ determined by the difference determining means 68, one or more abnormal time durations R-II, and removes the found abnormal time durations R-II from the 30 time durations R-II measured by the R-II-duration measuring means 50. As shown in FIG. 8, the differences $\Delta A$ obtained from the abnormal durations R-II can be clearly discriminated from those obtained from the normal durations R-II. For example, the abnormal-value removing means 72 judges whether each of the differences $\Delta A$ determined by the difference determining means 68 falls within a reference range, and judges, if the each difference $\Delta A$ does no fall within the reference range, that the time duration R-II from which the each difference $\Delta A$ has been obtained is abnormal. One or more time durations R-II judged as being abnormal are removed from the 30 time durations R-II. In the present embodiment, the removing means 72 determines the reference range based on a standard deviation, $\sigma$, from an average, $\Delta A_{AV}$, of the 30 differences $\Delta A$. The reference range may be the average $\Delta A_{AV} \pm$the standard deviation $\sigma$, or the average $\Delta A_{AV} \pm$twice the standard deviation, $2\sigma$.

An average determining means 74 determines an average, R-II$_{AV}$, of the measured time durations R-II from which one or more time durations R-II judged as being abnormal have already been removed by the abnormal-value removing means 72. For example, in the case where the abnormal-value removing means 72 removes one or more abnormal time durations R-II which do not fall within the reference range defined by the average$\pm$twice the standard deviation, i.e., $\Delta A_{AV} \pm 2\sigma$, as shown in FIG. 8, the removing means 72 removes, from the 30 time durations R-II shown in FIG. 4 or 5, the two abnormal time durations R-II indicated by the cross 58 and the triangle 60. In this case, the average determining means 74 determines an average of the 28 normal time durations R-II. The thus determined average indicates an accurate time of occurrence of the second heart sound II as measured from the R-wave of the ECG waveform. Based on the thus determined accurate time of occurrence of the second heart sound II, the control device 16 may determine a velocity, PWV, of propagation of a pulse wave, or a degree of arteriosclerosis, of the patient, in the manners described in Discussion of Related Art. Meanwhile, in the case where the reference range is defined by the average±the standard deviation, i.e., $\Delta A_{AV} \pm \sigma$, the removing means 72 removes, in addition to the two abnormal durations R-II indicated by the cross 58 and the triangle 60, the two normal durations R-II from all the 30 durations R-II, as shown in FIG. 8. In this case, the average determined from the 26 durations R-II is more accurate than that determined from the 30 durations R-II including the abnormal durations R-II indicated by the cross 58 and the triangle 60.

Figure 9:
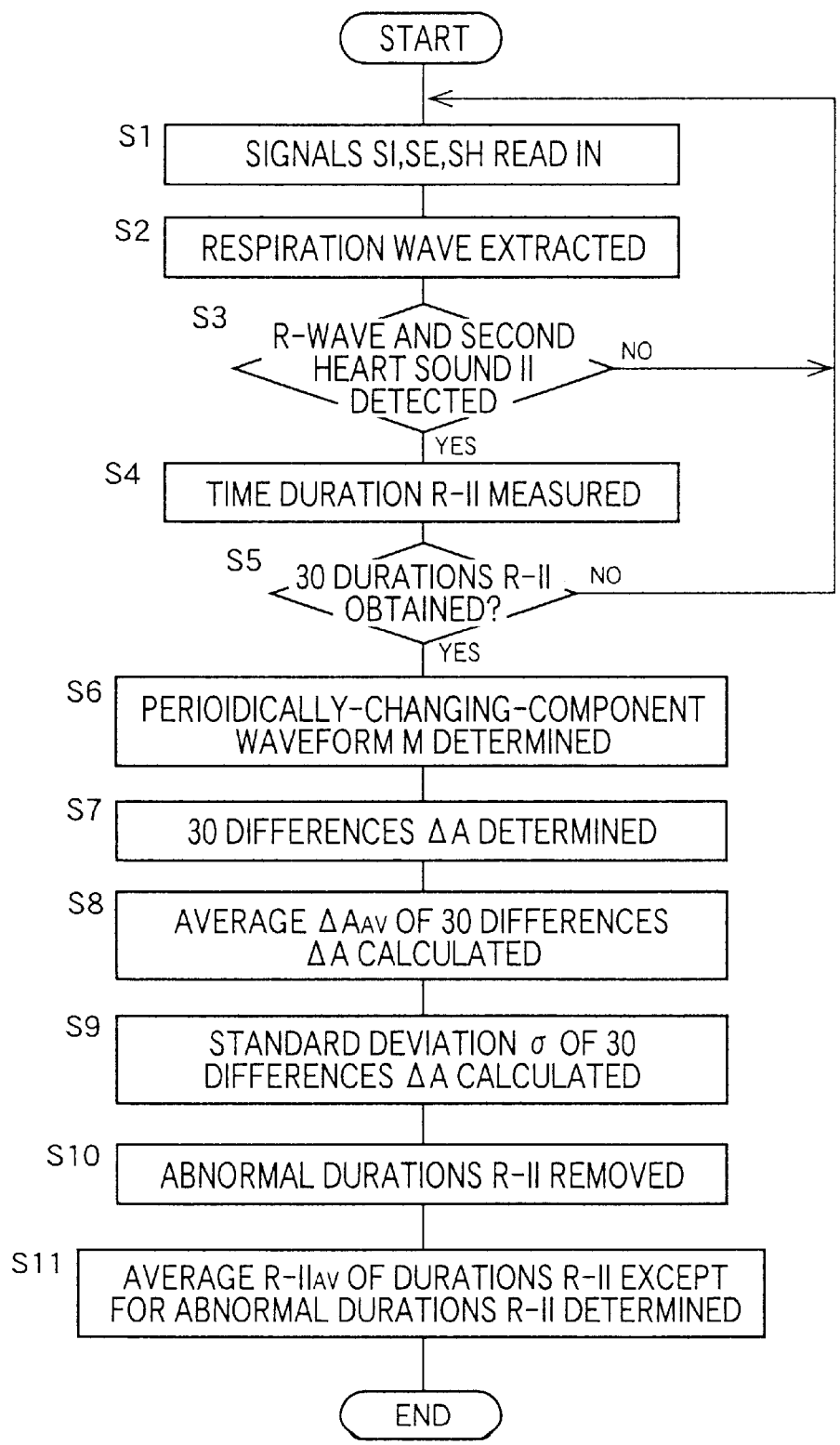
FIG. 9 is a flow chart representing a control program according to which the control device controls the apparatus of FIG. 1.
Figure 10A:
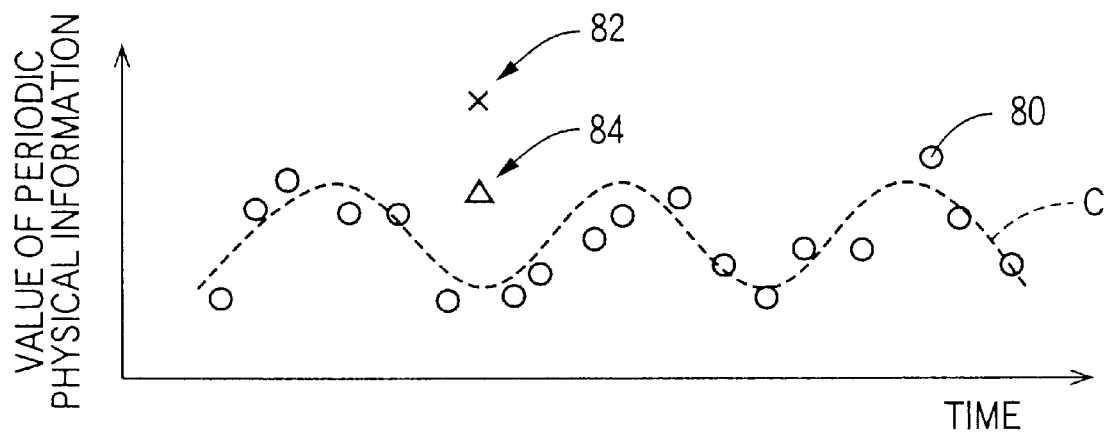
FIGS. 10A and 10B are views showing some abnormal values which are included in the measured values of periodic physical information but cannot be removed or discarded from the measured values.
Figure 10B:
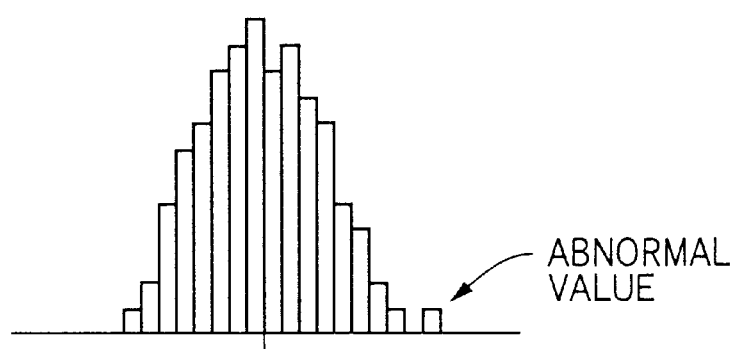

FIG. 9 is a flow chart representing the control program according to which the control device 16 controls the operation of the periodic-physical-information measuring apparatus 10. First, at Step S1, the control device 16 reads in the chest-impedance signal SI continuously supplied from the chest-impedance detecting device 18, the ECG signal SE continuously supplied from the ECG device 12, and the PCG signal SH continuously supplied from the heart-sound microphone 28.

Step S1 is followed by Step S2 corresponding to the respiration-wave detecting means 64. At Step S2, the control device 16 extracts, according to an respiration-wave extracting program pre-stored in the ROM 36, a respiration wave, f(t), having frequencies in a predetermined frequency band of from 0.1 to 0.5 Hz, as shown in the middle graph of FIG. 6, from the chest-impedance signal SI read in at Step S1.

Step S2 is followed by Step S3 to judge whether the ECG signal SE and the PCG signal SH read in at Step S1 include an R-wave and a second heart sound II, respectively. Steps S1 to Step S3 are repeated so long as negative judgments are made at Step S3. Meanwhile, if a positive judgment is made at Step S3, the control of the control device 16 goes to Step S4 corresponding to the periodic-physical-information measuring means 50. At Step S4, the control device 16 measures a time duration R-II from the time when the R-wave of the ECG signal SE is detected to a time when the start of the second heart sound II of the PCG signal SH is detected.

Step S4 is followed by Step S5 to judge whether the 30 time durations R-II corresponding to the 30 beats of the heart of the subject as the predetermined measurement interval have been determined at Step S4 since the commencement of the current measuring operation. If a negative judgment is made at Step S5, the control goes back to Step S1 and the following steps, so that the control device 16 additionally reads in the three signals SI, SE, SH.

Meanwhile, if a positive judgment is made at Step S5, the control goes to Step S6 corresponding to the periodically-changing-component-waveform (PCCW) determining means 66. At Step S6, the control device 16 determines a constant α as a coefficient of the respiration wave f(t), such that the sum of respective squares of respective differences between the 30 time durations R-II measured at respective times and respective products of the coefficient a and respective values of the respiration wave f(t) detected at the corresponding times, takes the least value. Based on the thus determined coefficient α, the control device 16 determines the waveform M of the periodically changing component of the 30 time durations R-II, i.e., M=αf(t) (β=0).

Step S6 is followed by Step S7 corresponding to the difference determining means 68. At Step S7, the control device 16 determines a difference ΔA between the value of each of the 30 time durations R-II measured at a time and a value of the periodically-changing-component waveform M at the same time. Thus, the control device 16 determines the 30 differences ΔA as shown in FIG. 7.

Step S7 is followed by Step S8 to calculate an average $\Delta A_{AV}$ of the 30 differences ΔA determined at Step S7, and then by Step S9 to calculate a standard deviation σ of the 30 differences ΔA determined at Step S7.

Step S9 is followed by Step S11 corresponding to the abnormal-value removing means 72. At Step S10, the control device 16 determines a reference range, i.e., $\Delta A_{AV} \pm 2\sigma$, and judges whether each of the 30 differences ΔA determined at Step S7 falls within the reference range. When the control device 16 finds one or more differences ΔA which do not fall within the reference range, the control device 16 judges that one or more time durations R-II from which the thus found one or more differences ΔA have been obtained, are abnormal because of erroneous measurement, and removes the one or more time durations R-II judged as being abnormal, from the 30 time durations R-II. Regarding the example shown in FIG. 4, the two abnormal time durations R-II indicated by the cross 58 and the triangle 60 are removed from the 30 time durations R-II.

Step S10 is followed by Step S11 corresponding to the average determining means 74. At Step S11, the control device 16 determines an average R-II$_{AV}$ of the 28 durations R-II obtained by removing the two durations R-II from the 30 durations R-II.

It emerges from the foregoing description that in the present embodiment, the R-II-duration measuring means 50 (Step S4) iteratively measures the 30 time durations R-II corresponding to the 30 beats of the heart of the living subject; the PCCW determining means 66 (Step S6) determines, based on the respiration wave f(t) detected by the respiration-wave detecting means 64 (Step S2), the waveform M of the periodically changing component contained in the 30 time durations R-II; the difference determining means 68 (Step S7) determines the respective differences ΔA between the respective values of the thirty time durations R-II measured at respective times and the respective values of the periodically-changing-component waveform M at the corresponding times; and the abnormal-value removing means 72 (Step S10) discriminates, based on the 30 differences ΔA, one or more abnormal durations R-II and removes the abnormal duration or durations R-II from the 30 time durations R-II measured by the R-II-duration measuring means 50. Thus, the present measuring apparatus 10 can easily remove or discard one or more abnormal durations R-II from the iteratively measured durations R-II.

In addition, the present measuring apparatus 10 includes the average determining means 74 (Step S11) which determines the average R-II$_{AV}$ of the time durations R-II from which one or more abnormal durations R-II resulting from erroneous measurement has or have been removed by the abnormal-value determining means 72. The thus determined average R-II$_{AV}$ is more accurate than an average of the 30 time durations R-II from which no abnormal durations R-II have been removed. Since the ECG waveform is not easily mixed with noise and accordingly is considerably accurately detected, the average R-II$_{AV}$ of the time durations R-II indicates an accurate time of occurrence of the second heart sound II as measured from the time of occurrence of the R-wave of the ECG waveform.

Moreover, the present measuring apparatus 10 includes the chest-impedance detecting device 18 which detects the chest-impedance pulse wave from the chest of the living subject, and the respiration-wave detecting means 64 (Step S2) which detects the respiration wave from the chest-impedance pulse wave detected by the detecting device 18. Since the chest-impedance pulse wave detected by the detecting device 18 contains the respiration-synchronous component, the respiration wave detected from the chest-impedance pulse wave enjoys a high accuracy.

While the present invention has been described in its preferred embodiment, the invention may otherwise be embodied.

For example, in the illustrated embodiment, the respiration-wave detecting means 64 (Step S2) detects, as the respiration wave, the respiration-synchronous component extracted from the chest-impedance pulse wave. However, it is possible to measure continuously a different sort of periodic physical information which is known as information which changes in synchronism with respiration of a living subject, such as intraarterial blood pressure or blood volume, and extract a respiration-synchronous component from the measured periodic physical information.

In the illustrated embodiment, the time durations R-II are iteratively measured as values of periodic physical information containing a periodically changing component resulting from respiration of a living subject, and one or more abnormal durations R-II are removed or discarded from the measured durations R-II. However, the principle of the present invention is applicable to other sorts of periodic physical information containing other sorts of periodically changing component than the periodically changing component resulting from the respiration of subject. For example, a pulse-wave propagation time, DT, which is needed for a pulse wave to propagate between two portions of a living subject, or a pulse-wave propagation velocity, PWV, corresponding one by one to the pulse-wave propagation time DT is known as periodic physical information containing a periodically changing component resulting from fluctuations of the autonomic serve system of the subject. Therefore, the present invention is applicable to the pulse-wave propagation time DT and the pulse-wave propagation velocity PWV. In this connection, it is noted that the fluctuations of autonomic serve system of a living subject contain a high-frequency component, HF, having substantially the same frequency as that of the respiration of the subject, and a low-frequency component, LF, having a frequency equal to from one third to one fourth of the frequency of respiration.

In the case where the present invention is applicable to the measurement of pulse-wave propagation time DT, one or more abnormal values are removed from iteratively measured values of the propagation time DT, as follow: First, the periodic-physical-information measuring means 50 iteratively measures a value of the propagation time DT based on respective pulse waves detected by two pulse-wave sensors which are worn on two different portions of a living subject. Second, the PCCW determining means 66 determines a waveform, M(t), of a periodically changing component contained in the iteratively measured values of the time DT. This periodically changing component corresponds to that of the fluctuations of autonomic nerve system, i.e., the high-frequency or low-frequency component HF, LF. To this end, values of pulse period, RR, blood pressure BP (diastolic BP value $BP_{DIA}$, mean BP value $BP_{MEAN}$, or systolic BP value $BP_{SYS}$), or pulse pressure known as periodic physical information containing a periodically changing component corresponding to that of the fluctuations of autonomic nerve system are iteratively measured and, as described in the illustrated embodiment, the constants α, β of the expression (1) are so determined that the sum of respective squares of respective differences between respective values of the time DT measured at respective times and respective values of a waveform, f(t), obtained by connecting the respective measured pulse period values RR (or BP values BP, or pulse pressure values) take the least value. Thus, the waveform M(t) of periodically changing component is determined. Here, it is noted that a pulse pressure value is defined as the difference between systolic and diastolic BP values determined for each heartbeat-synchronous pulse of a living subject.

In the illustrated embodiment, the abnormal-value removing means 72 (Step S10) judges whether each of the measured time durations R-II is abnormal by judging whether the corresponding difference ΔA falls within the reference range, ΔAAV±2σ. However, any of other sorts of statistical-analysis techniques that are widely used in the art may be used to discriminate one or more abnormal differences from the determined differences ΔA and remove one or more corresponding abnormal durations from the measured durations R-II. Those statistical-analysis techniques are, for example, Leverage, Cook's distance, Welch distance, Covatio, and Dfbeta.

In the illustrated embodiment, the two electrodes 14 are placed on the chest of the living subject to detect the chest-impedance pulse wave from the subject. However, the two electrodes 14 may not be placed on the chest, so long as the two electrodes 14 "sandwich" the chest. For example, the two electrodes 14 may be placed on right-hand and left-hand wrists, respectively.

In the illustrated embodiment, the R-II-duration measuring means 50 iteratively measures the time durations R-II in a measurement interval predetermined based on the number of beats of the heart of the subject, i.e., 30 time durations R-II corresponding to 30 beats of the heart of the subject. However, the measurement interval may be predetermined as a time which elapses from the start of the measurement.

Moreover, in the illustrated embodiment, the respiration-wave detecting means 64 is provided by the software (i.e., program) which is pre-stored in the ROM 36 of the control device 16. However, the respiration-wave detecting means 64 may be provided by hardware. For example, the detecting means 64 may be provided by a band-pass filter which extracts a signal component having frequencies in a frequency band of 0.1 to 0.5 Hz and which is disposed between the detector circuit 24 and the A/D converter 26.

It is to be understood that the present invention may be embodied with other changes, modifications and improvements which may occur to a person skilled in the art, without departing from the spirit and scope of the invention defined in the appended claims.

What is claimed is:

1. An apparatus for measuring a periodic physical information of a living subject, comprising:

a measuring device which iteratively measures, from the subject, a value of the periodic physical information comprising a periodically changing component;

a waveform determining means for determining a changing-component waveform representing the periodically to changing component of the periodic physical information;

a difference determining means for determining at least one difference between at least one first value of the periodic physical information measured by the measuring device at at least one time and at least one second value of the changing-component waveform at said at least one time; and a removing means for judging, based on said at least one difference determined by the difference determining means, whether said at least one first value is abnormal, and removing said at least one first value judged as being abnormal.

2. An apparatus according to claim 1, further comprising an average determining means for determining an average of the iteratively measured values of the periodic physical information from which said at least one first value judged as being abnormal has been removed.

3. An apparatus according to claim 1, wherein the removing means comprises judging means for judging whether each one of the iteratively measured values of the periodic physical information falls within a reference range and, if said each measured value does not fall within the reference range, judging that said each one measured value is abnormal.

4. An apparatus according to claim 3, wherein the removing means further comprising means for determining an average and a standard deviation of the iteratively measured values of the periodic physical information, and means for determining the reference range based on the determined average and standard deviation.

5. An apparatus for measuring a periodic physical information of a living subject, comprising:
   a measuring device which iteratively measures, from the subject, a value of the periodic physical information comprising a periodically changing component resulting from a respiration of the subject;
   a respiration-wave detecting device which detects a respiration wave resulting from the respiration of the subject;
   a waveform determining means for determining, based on the respiration wave detected by the respiration-wave detecting device, a changing-component waveform representing the periodically changing component of the periodic physical information;
   a difference determining means for determining at least one difference between at least one first value of the periodic physical information measured by the measuring device at at least one time and at least one second value of the changing-component waveform at said at least one time; and
   a removing means for judging, based on said at least one difference determined by the difference determining means, whether said at least one first value is abnormal, and removing said at least one first value judged as being abnormal.

6. An apparatus according to claim 5, further comprising an average determining means for determining an average of the iteratively measured values of the periodic physical information from which said at least one first value judged as being abnormal has been removed.

7. An apparatus according to claim 5, wherein the measuring device comprises:
   an electrocardiograph device which includes a plurality of electrodes adapted to be placed on a plurality of body portions of the subject, continuously detects an electrocardiogram waveform, from the subject through the electrodes, and outputs an electrocardiogram-waveform signal representing the detected electrocardiogram waveform;
   a heart-sound sensor which detects a plurality of second heart sounds, II, produced from the heart of the subject, and outputs a heart-sound signal representing the detected second heart sounds II; and
   a measuring means for iteratively measuring a time difference between a first time when a predetermined periodic point on the electrocardiogram waveform is detected by the electrocardiograph device and a second time when a start point of each of the second heart sounds II is detected by the heart-sound sensor.

8. An apparatus according to claim 5, wherein the waveform determining means comprises means for determining, based on the respiration wave, f(t), detected by the respiration-wave detecting device, the changing-component waveform, M, of the periodic physical information, as follows:

$$M = \alpha f(t) + \beta$$

where $\alpha$ and $\beta$ are constants.

9. An apparatus according to claim 5, wherein the respiration-wave detecting device comprises:
   a chest-impedance-pulse-wave detecting device which detects a chest-impedance pulse wave from a chest of the subject; and
   an extracting means for extracting the respiration wave from the chest-impedance pulse wave detected by the chest-impedance-pulse-wave detecting device.

10. An apparatus according to claim 9, wherein the extracting means of the respiration-wave detecting device comprises means for extracting the respiration wave having frequencies in a predetermined frequency band, from the chest-impedance pulse wave detected by the chest-impedance-pulse-wave detecting device.

* * * * *